United States Patent
Hauswald

(10) Patent No.: US 8,920,382 B1
(45) Date of Patent: Dec. 30, 2014

(54) PATIENT CONTROLLED ANALGESIA DEVICE

(71) Applicant: Mark Hauswald, Telluride, CO (US)

(72) Inventor: Mark Hauswald, Telluride, CO (US)

(73) Assignee: STC.UNM, Albuquerque, NM (US)

( * ) Notice: Subject to any disclaimer, the term of this patent is extended or adjusted under 35 U.S.C. 154(b) by 130 days.

(21) Appl. No.: 13/815,405

(22) Filed: Feb. 28, 2013

Related U.S. Application Data

(60) Provisional application No. 61/607,832, filed on Mar. 7, 2012.

(51) Int. Cl.
*A61M 5/178* (2006.01)
*A61M 5/315* (2006.01)

(52) U.S. Cl.
CPC ....... *A61M 5/31535* (2013.01); *A61M 5/31548* (2013.01)
USPC ........................................................ 604/183

(58) Field of Classification Search
CPC ... A61M 5/14; A61M 5/141; A61M 5/14212; A61M 5/14216; A61M 5/1422; A61M 5/1424; A61M 5/145; A61M 5/1452; A61M 5/1456; A61M 5/14566; A61M 5/204; A61M 2005/1405; A61M 2005/14506
USPC ......... 604/125, 131, 181, 183, 186, 187, 220, 604/227, 229
See application file for complete search history.

(56) References Cited

U.S. PATENT DOCUMENTS

| | | | |
|---|---|---|---|
| 6,270,481 B1 * | 8/2001 | Mason et al. | 604/181 |
| 6,719,728 B2 * | 4/2004 | Mason et al. | 604/181 |
| 8,016,790 B2 * | 9/2011 | Walborn et al. | 604/153 |
| 8,308,457 B2 | 11/2012 | Goldor | |
| 2007/0299408 A1 * | 12/2007 | Alferness et al. | 604/250 |

FOREIGN PATENT DOCUMENTS

| | | | |
|---|---|---|---|
| EP | 1545656 A1 | 6/2005 | |
| EP | 1242134 B1 | 6/2006 | |

* cited by examiner

*Primary Examiner* — Kami A Bosworth
*Assistant Examiner* — Glen Janson

(57) ABSTRACT

A mechanical patient-controlled analgesia device for injecting medicine into a patient's IV, includes an IV reservoir and a syringe communicated to the IV reservoir and having a syringe plunger. A mechanical biasing element is provided for exerting bias on the syringe plunger in a first syringe-filling direction to draw medicine from the IV reservoir into the syringe. An injection plunger is operable by the patient to move the syringe plunger in a second injection direction against the bias to inject the medicine in the syringe into a patient's IV. The injection plunger is movable independently of the syringe plunger and is engaged with but unconnected to the syringe plunger when the patient moves the injection plunger to inject the medicine. The patient can inject only a calibrated amount of medicine drawn into the syringe as determined by calibration of the biasing element and a metering element for a given viscosity of the medication.

23 Claims, 2 Drawing Sheets

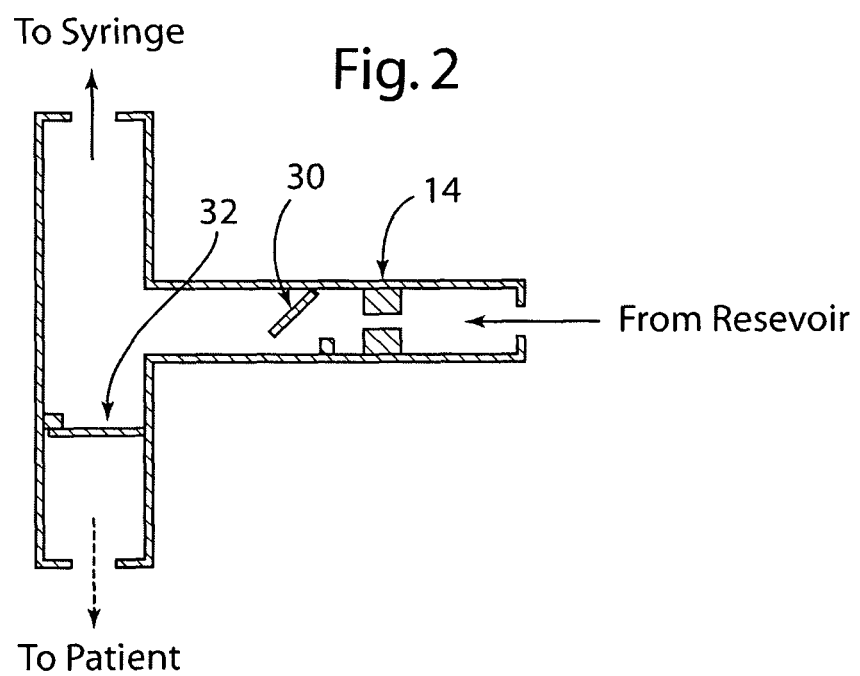

PATIENT CONTROLLED ANALGESIA DEVICE

RELATED APPLICATION

This application claims benefits and priority of U.S. provisional application Ser. No. 61/607,832 filed Mar. 7, 2012, the entire disclosure of which is incorporated herein by reference.

FIELD OF THE INVENTION

This invention relates generally to a patient controlled analgesia (PCA) device and, more specifically, to a mechanical, low cost, and disposable PCA that allows a patient to titrate their own pain medication.

BACKGROUND OF THE INVENTION

Pain is common in emergency medicine. The most effective drugs for severe pain are narcotic analgesics. Narcotics must be given intravenously in order to have rapid effect. Narcotics have idiosyncratic effects and their effects vary widely between patients. Therefore, it is difficult to predict what dose is appropriate for a specific patient.

Narcotics are most commonly used to ease pain and are (and most appropriately) titrated to effect. This means that small doses are given frequently until the patient has an adequate response. Since pain relief and most side effects are subjective, this means that doses are continued until the patient stops requesting more and says they have had enough. In practice, this procedure is difficult and time consuming; as a result, most patients do not receive optimal doses, because if the doses are made small enough and the intervals between them long enough to be safe, titration can easily take a half hour. Because of lengthy titration periods, either a nurse or other provider stays at the bedside during the entire period or the titration is slowed (meaning longer without pain relief) or larger doses/shorter time periods are used (which decreases safety). Using morphine as an example, 2 mg (a safe dose) every 3 minutes (just long enough to get from arm to brain) to 20 mg (a reasonable loading dose) takes 30 minutes.

There is also considerable evidence that when medical staff give pain medications only when patients ask, the patients rarely get enough; a condition known as oligo-analgesia. Worse, this often results in intermittent overdosing. Patients commonly alternate between pain and over sedation when these "prn" orders are used.

The solution to this problem is Patient Controlled Analgesia machines, or PCAs. Current PCAs are electro mechanical devices that patients use to inject their own pain medications when they want them. PCAs reduce both oligo-analgesia and sedation, and patients use less narcotics overall and recover faster.

PCAs are the standard of care on post-operative units, but are rarely used in emergency departments or similar areas. This is because PCAs are quite complicated. PCAs must be individually programmed for each patient. Programming must include dose and interval between doses plus a "lockout" period. For example: the protocol might be "morphine sulphate, 2 mg every 5 minutes but no more than 10 mg per hour or 20 mg every 4 hours". This is necessary and useful during a prolonged post-operative stay, particularly since patients are loaded with medication in the post anesthesia recovery area prior to moving to the ward. In addition, PCAs require the medication to be used in a specific container; in this case morphine might be available only in a 30 mg pre filled vial specific for the kind of PCA machine used. For obvious reasons, PCAs require redundancy and fail safe mechanisms. As a result, PCA's are expensive, fragile, and time consuming to set up.

What is needed is a PCA that is specific to the needs of the emergency patient. Since emergency patients start with no pain medication, and because they rarely stay for more than a few hours, what is really needed is a device that they can use to titrate their own loading dose. For emergency patients, maintenance doses are not the issue that they are for admitted patients. The device needs to be quick and easy to set up and use so patients do not need to wait in pain for programming to take place.

SUMMARY OF THE INVENTION

To this end, the present invention provides a patient-controlled analgesia (PCA) device, especially for use with emergency patients, although the invention is not limited to emergency patient use. In an illustrative embodiment of the present invention, PCA device comprises an IV (intravenous) medication reservoir, a syringe communicated to the reservoir and having a syringe plunger, a biasing element, such as for example a compression spring, for exerting bias on the syringe plunger in a first, syringe-filling direction to draw medication from the IV reservoir into the syringe, and an injection plunger operable by the patient to move the syringe plunger in a second injection direction against the bias to inject the medication in the syringe into a patient's IV. The injection plunger is movable independently of the syringe plunger and is engaged with but unconnected to the syringe plunger when the patient moves the injection plunger to inject the medication. As a result, the patient can use the injection plunger to inject the calibrated amount of medication in the syringe into the patient's IV but cannot use the injection plunger to draw medication from the IV reservoir into the syringe.

In a particular embodiment of the present invention, the syringe is communicated to the IV medication reservoir by a metering element and has a syringe plunger which travels under bias of the biasing element in the first, syringe-filling direction to draw medicine from the IV medication reservoir into the syringe wherein the metering element and the biasing spring are calibrated to permit a only calibrated amount of medication to be drawn for a given time into the syringe from the IV medication reservoir. The patient can inject only this calibrated amount of medication into the patient's IV since the calibrated amount is determined by the biasing element and metering element for a given viscosity of the medication.

The present invention also envisions a PCA method of injecting medicine into a patient's IV comprising the steps of drawing medicine from an IV medication reservoir into a syringe using a biasing element that exerts bias on a plunger of the syringe in a first, syringe-filling direction to draw medication into the syringe and then injecting the medicine in the syringe into the patient's IV by the patient's operating the injection plunger that engages but is unconnected to the syringe plunger to move the syringe against the bias in a second injection direction.

The PCA device and method pursuant to the present invention are advantageous especially for use by the emergency patient. The PCA device and method provides quick and easy set-up and use. Since emergency patients start with no pain medication, and because they rarely stay for more than a few hours, the patient can use the PCA device to titrate their own loading dose so the patient does not need to wait in pain for programming to take place.

These and other advantages will become more apparent from the following detailed description taken with the following drawings.

BRIEF DESCRIPTION OF THE DRAWINGS

FIG. 2 is an enlarged schematic view of the IV medication reservoir metering element and one-way valves when fluid/medication is being drawn from the reservoir into the syringe (valve from reservoir is open and valve to patient is closed).

DETAILED DESCRIPTION OF THE INVENTION

Figure 1:
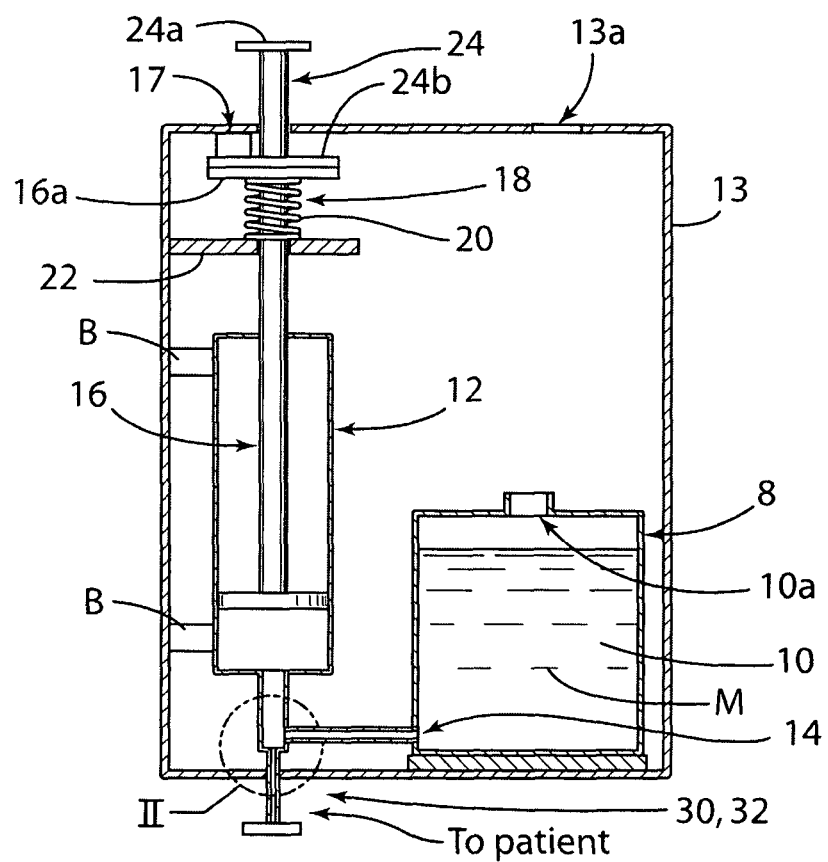
FIG. 1 shows an illustrative embodiment of a mechanical PCA, according to an illustrative embodiment of the present invention.

FIGS. 1 and 2 schematically depict an illustrative embodiment of the mechanical PCA offered for purposes of illustration and not limitation as comprising a medication reservoir 8, such as, for example, a conventional IV medication bag 10, and a conventional syringe 12 communicated to the IV bag 10. The IV bag 10 is disposed in the container 13 and shown supported on the container bottom for purposes of illustration and not limitation. The syringe 12 is disposed in the container 13 and is fixedly supported by brackets B or other support in container 13. The container 13 includes an opening 13a that allows ambient air to flow into and out of container 13 and a closeable door (not shown).

The IV reservoir 10 is filled via injection port 10a with medication or is preloaded with medication. The container door can be latched shut after a preloaded bag is in position or after medicine is added to the IV bag in the container. The IV reservoir 10 also includes or is connected to a metering element 14 that participates in flow rate control of the medication in the IV reservoir into the syringe as explained below. For purposes of illustration and not limitation, the IV reservoir 10 can be a commercially available IV bag. The metering element 14 can comprise, but is not limited to, a capillary tube, a metering needle valve, or a combination thereof.

The syringe 12 includes a syringe plunger 16 which is biased by a spring biasing element 18 in an upward (first) syringe-filling direction to draw fluid medicine from the IV reservoir 10 into the syringe when the syringe plunger 16 is moved upwardly. The metering element 14 and the biasing element 18 are calibrated to permit a calibrated amount of medication to be drawn for a given time (e.g. 5 ml in two minutes) into the syringe from the IV medication reservoir. For purposes of illustration and not limitation, the syringe 12 with plunger 16 can be a commercially available syringe.

For purposes of illustration, the biasing element 18 is shown comprising a compression coil spring 20, which resides around the shaft of the syringe plunger 16 and between an outer spring retainer end 16a of the syringe plunger 16 and a fixed spring support member 22, which is affixed to the container 13. However, the biasing element 18 can comprise an elastic or resilient plastic or rubber sleeve, or other biasing element that can exert an upward bias on the syringe plunger 16 in FIG. 1.

Referring to FIG. 1, a patient-operated injection plunger 24 is shown disposed above the syringe plunger 16 and operable by the patient to move the syringe plunger 16 in a downward injection (second) direction against the bias of the biasing element 18 to inject the medication in the syringe into a patient's IV. The injection plunger 24 is movable upwardly and downwardly independently of the syringe plunger 16 and is engaged with but unconnected to the syringe plunger 16 when the patient moves the injection plunger to inject the medicine. To this end, the injection plunger 24 includes an outer patient-operable end 24a disposed outside the container 13 and an inner lower end 24b inside the container 13 that engages but is unconnected to outer upper end 16a of the syringe plunger 16. The inner lower end 24b of the injection plunger 24 rests on, but is unconnected to, the outer upper spring retainer end 16a of the syringe plunger 16 so as to follow its movement up and down in response to bias of the biasing element 18 (spring 20), except when the patient pushes the injection plunger 24 downwardly or pulls it upwardly. The inner lower end 24b of the injection plunger during its upward movement eventually abuts a stop 17 that is fixedly disposed on the container.

The IV medication reservoir 10 is connected or communicated to syringe 12 via a one way valve 30 that allows the biasing element 18 to draw medicine from the reservoir 10, but closes under pressure so that fluid medication does not flow from syringe 12 to back to the IV reservoir 10 and a second one way valve 32 that allows the syringe plunger 16 to push medication from the syringe 12 into patient's IV but prevents flow of IV fluid/medication from the patient's IV back into the syringe. FIG. 2 illustrates schematically the one way flapper valves 30 and 32 and metering element 14. The one-way valves 30, 32 can include, but are not limited to, ball check valves, conical check valves, or flapper valves.

In practice of a method embodiment of the present invention, the IV medication reservoir 10 is filled via injection port 10a with medication and injection fluid as needed (collectively designated M in FIG. 1) and connected to syringe 12 via metering element 14 and one way valves 30 and 32. The door of box or container 13 is closed and locked. The biasing element 18 (e.g. compression spring 20) and metering element 14 (e.g. capillary tube) are calibrated to allow a specific amount of medicine to flow into the syringe per unit time (e.g., 5 ml in two minutes), corresponding to a maximum amount of medication ordered per unit time. Different mechanical PCAs can be designed to give different volumes of fluid with each injection, and the biasing element 18 (e.g. spring 20) and metering element 14 are calibrated for each one.

Thus, the mechanical properties of the illustrated PCA device (e.g. spring, capillary tube radius for a given fluid viscosity) limit the dose per time interval. The difference between the height of the spring biasing element 20 when fully compressed and the height of the spring biasing element 20 when fully extended as determined by the fixed stop 17 determines the maximum amount of medication drawn into the syringe 12, and hence the maximum dose injected at one time. A different spring/metering element (restrictor) combination can be selected and used in order to adjust the particular volume of fluid/medication for each injection. The biasing element 18 (e.g. spring 20) and metering element (restrictor) 14 are calibrated for each combination.

The syringe 12 cannot fill more rapidly than the biasing element 18 (spring 20) and restricting needle or capillary tube allow for a given fluid viscosity of the medication. Even doubling the spring force alone has relatively little effect on filling time. The injection plunger 24 touches, but does not connect to, the syringe plunger 16, so drawing the injection plunger back (upwardly in FIG. 1) does not fill the syringe. Since the viscosity of water soluble medications approximate that of water a single biasing element and metering element (restrictor) combination can be used for multiple medications.

Once the syringe is filled, the patient simply pushes the injection plunger 24 downwardly to inject the calibrated amount of medication into the patient's IV. Since the injection plunger 24 is not connected to the syringe plunger 16, the injection plunger cannot be used to pull medication into the syringe 12. Thus, the patient's pressing on the injection plunger cannot cause more than the specified amount of medication to be injected per unit time.

The PCA device described above may be fabricated of conventional medical parts (syringe, restricting needle, connecting tubing, valves and IV medication bag), but using components specifically designed for the PCA device could make it simpler and easier to set up. The PCA device thus can be very low cost and hence disposable. The above-described embodiments of the PCA device do not comprise any electrical or electro-mechanical parts, although such parts may be incorporated into the PCA device. For example, the biasing element 18 may be replaced by an electrical or electromechanical (solenoid) biasing device.

The PCA device has potential uses in pre-hospital (ambulance) care, acute/urgent care clinics, emergency departments and other sites where loading doses of medications are given to treat acute pain and prior to painful procedures.

It is noted that, as used in this specification and the appended claims, the singular forms "a," "an," and "the," include plural referents unless expressly and unequivocally limited to one referent. Thus, for example, reference to "a PCA" includes two or more different PCAs. As used herein, the term "include" and its grammatical variants are intended to be non-limiting, such that recitation of items in a list is not to the exclusion of other like items that can be substituted or other items that can be added to the listed items.

Upon studying the disclosure, it will be apparent to those skilled in the art that various modifications and variations can be made in the devices and methods of various embodiments of the invention. Other embodiments will be apparent to those skilled in the art from consideration of the specification and practice of the embodiments disclosed herein. It is intended that the specification and examples be considered as examples only. The various embodiments are not necessarily mutually exclusive, as some embodiments can be combined with one or more other embodiments to form new embodiments.

I claim:

1. A patient-controlled analgesia device, comprising an IV medication reservoir, a syringe communicated to the IV medication reservoir and having a syringe plunger, a biasing element for exerting bias on the syringe plunger in a first syringe-filling direction to draw medication from the IV medication reservoir into the syringe, and an injection plunger operable by the patient to move the syringe plunger in a second injection direction against the bias to inject the medication in the syringe into a patient's IV, said injection plunger being movable independently of the syringe plunger and being engaged with but unconnected to the syringe plunger when the patient moves the injection plunger to inject the medication.

2. The device of claim 1 further including a one-way valve to prevent medication from being transferred from the syringe back into the IV medication reservoir when the syringe plunger is moved in the second injection direction.

3. The device of claim 1 further including a second one-way valve to prevent flow of medication from the patient's IV back to the syringe.

4. The device of claim 1 wherein the injection plunger includes a patient-operable end and an opposite end that engages but is unconnected to an outer end of the syringe plunger when the patient moves the injection plunger to inject the medication.

5. The device of claim 1 wherein the syringe plunger includes an outer end spaced from a fixed support member, the biasing element being disposed between the outer end of the syringe plunger and the fixed support member.

6. The device of claim 1 wherein the biasing element is a compression spring.

7. The device of claim 1 further including a container in which the IV medication reservoir, the syringe, and the biasing element are enclosed.

8. The device of claim 7 wherein the injection plunger includes an outer patient-operable end disposed outside the container and an inner end inside the container that engages but is unconnected to the syringe plunger.

9. The device of claim 7 wherein the container includes an opening to admit air into the container.

10. A patient-controlled analgesia device, comprising an IV medication reservoir, a syringe communicated to the IV medication reservoir by a metering element and having a syringe plunger, a mechanical biasing element for exerting bias on the syringe plunger to move it in a first syringe-filing direction to draw medication from the IV medication reservoir into the syringe wherein the metering element and the biasing spring are calibrated to permit a calibrated amount of medication to be drawn for a given time into the syringe from the IV medication reservoir, and an injection plunger operable by the patient to move the syringe plunger in a second opposite injection direction against the bias to inject the medication in the syringe into a patient's IV, said injection plunger being movable independently of the syringe plunger and being engaged with but unconnected to the syringe plunger when the patient moves the injection plunger to inject the medication.

11. The device of claim 10 further including a one-way valve to prevent medication from being transferred from the syringe back into the IV medication reservoir when the syringe plunger is moved in the second opposite injection direction.

12. The device of claim 10 further including a second one-way valve to prevent flow of medication from the patient's IV back to the syringe.

13. The device of claim 10 wherein the injection plunger includes a patient-operable end and an opposite end that engages but is unconnected to an outer end of the syringe plunger when the patient moves the injection plunger to inject the medication.

14. The device of claim 10 wherein the syringe plunger includes an outer end spaced from a fixed support member, the mechanical biasing element being disposed between the outer end of the syringe plunger and the fixed support member.

15. The device of claim 10 wherein the biasing element is a compression spring.

16. The device of claim 10 further including a container in which the IV medication reservoir, the syringe, and the mechanical biasing element are enclosed.

17. The device of claim 16 wherein the injection plunger includes an outer patient-operable end disposed outside the container and an inner end that engages but is unconnected to the syringe plunger.

18. The device of claim 16 wherein the container includes an opening to admit air into the container.

19. A patient-controlled analgesia device, comprising an IV medication reservoir, a syringe communicated to the IV medication reservoir by a metering element and having a syringe plunger which is biased by a spring biasing element in an upward syringe-filling direction to draw medication from the IV medication reservoir into the syringe wherein the metering element and the spring biasing element are calibrated to permit a calibrated amount of medication to be drawn for a given time into the syringe from the IV medication reservoir, an injection plunger disposed above the syringe plunger and operable by the patient to move the syringe plunger in a downward injection direction against the bias to inject the medication in the syringe into a patient's IV, said injection plunger being movable independently of the syringe plunger and being engaged with but unconnected to the syringe plunger, and a one-way valve to prevent medication from being transferred from the syringe back into the IV medication reservoir when the syringe plunger is moved in the downward injection direction.

20. The device of claim 19 further including a second one-way valve to prevent flow of medication from the patient's IV back to the syringe.

21. The device of claim 19 further including a container in which the IV medication reservoir, the syringe, and the spring biasing element are enclosed.

22. The device of claim 21 wherein the injection plunger includes an outer patient-operable end disposed outside the container and an inner end inside the container that engages but is unconnected to the syringe plunger.

23. The device of claim 21 wherein the container includes an opening to admit air into the container.

* * * * *